(12) United States Patent
Edney et al.

(10) Patent No.: US 8,519,138 B2
(45) Date of Patent: Aug. 27, 2013

(54) PROCESS FOR THE PREPARATION OF A BIPHENYL-2-YL CARBAMIC ACID ESTER

(75) Inventors: Dean David Edney, Stevenage (GB); Matthew Peter John, Stevenage (GB)

(73) Assignee: Glaxo Group Limited, Greenford, Middlesex (GB)

( * ) Notice: Subject to any disclaimer, the term of this patent is extended or adjusted under 35 U.S.C. 154(b) by 142 days.

(21) Appl. No.: 13/263,857

(22) PCT Filed: Apr. 14, 2010

(86) PCT No.: PCT/EP2010/054893
§ 371 (c)(1),
(2), (4) Date: Oct. 11, 2011

(87) PCT Pub. No.: WO2010/119064
PCT Pub. Date: Oct. 21, 2010

(65) Prior Publication Data
US 2012/0046469 A1    Feb. 23, 2012

Related U.S. Application Data

(60) Provisional application No. 61/169,046, filed on Apr. 14, 2009.

(51) Int. Cl.
*C07D 211/46* (2006.01)
*C07C 233/55* (2006.01)

(52) U.S. Cl.
USPC .......................................... 546/222; 564/207

(58) Field of Classification Search
USPC .......................................... 546/222; 564/207
See application file for complete search history.

(56) References Cited

U.S. PATENT DOCUMENTS

| | | | | |
|---|---|---|---|---|
| 7,317,102 | B2 * | 1/2008 | Mammen et al. | 546/176 |
| 7,345,175 | B2 * | 3/2008 | Mammen et al. | 546/242 |
| 7,842,704 | B2 * | 11/2010 | Mammen et al. | 514/323 |
| 8,143,277 | B2 * | 3/2012 | Mammen et al. | 514/312 |

FOREIGN PATENT DOCUMENTS
WO    2006/023454 A    3/2006

OTHER PUBLICATIONS
PCT/EP2010/054893 "Form 237 written opinion" (2010).*

* cited by examiner

*Primary Examiner* — Celia Chang
(74) *Attorney, Agent, or Firm* — Robert J. Smith

(57) ABSTRACT

A novel process for the preparation of the compound of formula (II):

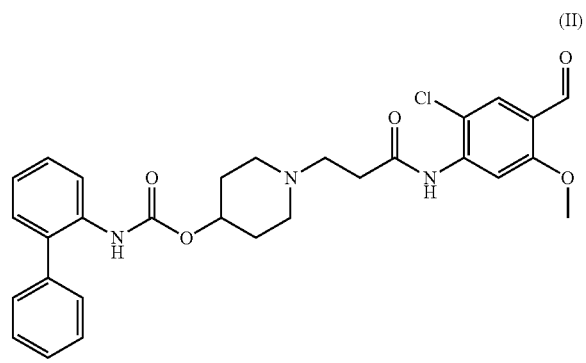

which process comprises reacting a compound of formula (VI):

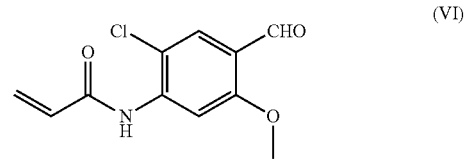

with a compound of formula (IV):

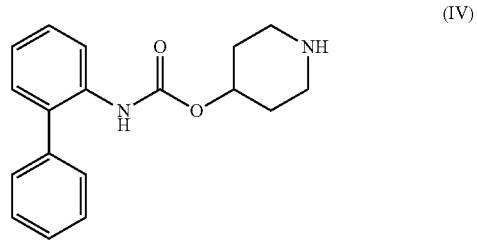

in a suitable solvent.

13 Claims, No Drawings

PROCESS FOR THE PREPARATION OF A BIPHENYL-2-YL CARBAMIC ACID ESTER

This application is filed pursuant to 35 U.S.C. §371 as a United States National Phase Application of International Application No. PCT/EP2010/054893 filed Apr. 14, 1010, which claims priority from U.S. Provisional 61/169046 filed Apr. 14, 2009.

The present invention relates to a novel, key step in the process for preparing biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester, which possesses both muscarinic antagonist and β₂ adrenergic receptor agonist activity.

International Patent application WO 2004/074246 (Theravance Inc, South San Francisco, Calif., US), filed on 13 Feb. 2004, discloses novel biphenyl compounds that are useful in the treatment of pulmonary disorders, such as chronic obstructive pulmonary disease (COPD) and asthma. In particular, the compound, biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester is disclosed as possessing both muscarinic antagonist and β₂ adrenergic receptor agonist activity. The chemical structure of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester is represented by formula (I):

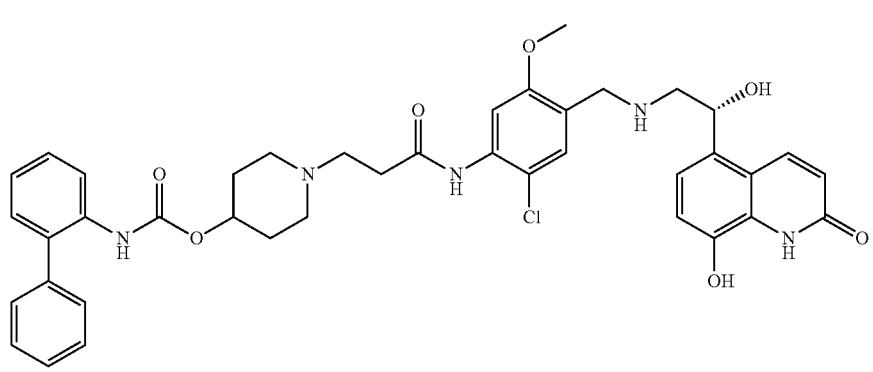

(I)

WO 2004/074246 discloses a process for the preparation of the compound of formula (I).

An important intermediate in the preparation of the compound of formula (I) is biphenyl-2-ylcarbamic acid 1-[2-(2-chloro-4-formyl-5-methoxyphenyl-carbamoylethyl] piperidin-4-yl ester (also known as 1-(3-{[2-chloro-4-formyl-5-(methyloxy)phenyl]amino}-3-oxopropyl)-4-piperidinyl 2-biphenylylcarbamate), represented by formula (II):

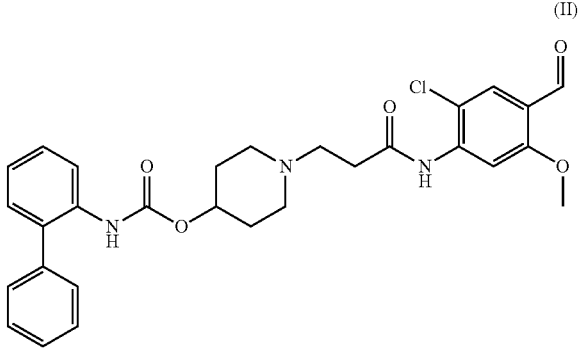 [SMILES: COc1cc(NC(=O)CCN2CCC(OC(=O)Nc3ccccc3-c3ccccc3)CC2)c(Cl)cc1C=O]

A key step, disclosed in WO 2004/074246 (Preparation 95), in the preparation of the compound of formula (II) is the reaction of methyl 4-(acryloylamino)-5-chloro-2-(methyloxy)benzoate, represented by formula (III):

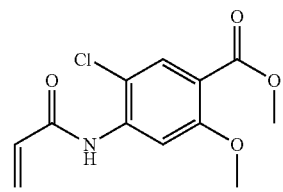

with biphenyl-2-ylcarbamic acid piperidin-4-yl ester, represented by formula (IV):

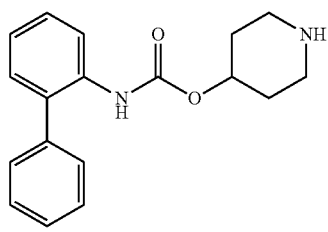

to yield methyl 4-{3-[4-(biphenyl-2-ylcarbamoyloxy)piperidin-1-yl]propionylamino}-5-chloro-2-methoxybenzoate, represented by formula (V).

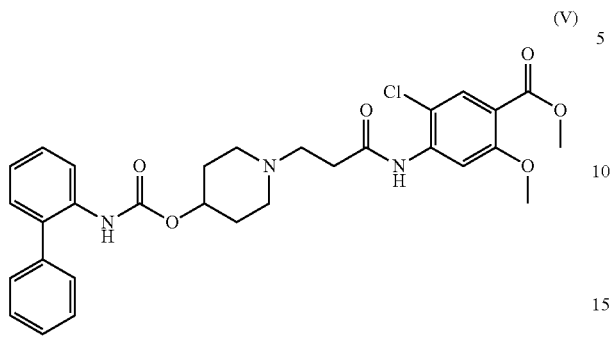

(V)

In this reaction the compound of formula (III) is at the ester oxidation level. Consequently, WO 2004/074246 outlines two further reaction steps that are required for conversion of the compound of formula (V) to the compound of formula (II), formulae for which are both outlined above. Firstly, a reduction to the alcohol oxidation level, and secondly, an oxidation to the aldehyde oxidation level. Thus, starting with the coupling reaction between the compound of formula (III) and the compound of formula (IV), three process steps were required for the preparation of the key intermediate biphenyl-2-ylcarbamic acid 1-[2-(2-chloro-4-formyl-5-methoxyphenyl-carbomoylethyl]piperidin-4-yl ester.

In two more recent International patent applications, WO 2006/023454 and WO 2007/090859, three step processes are again disclosed for the preparation of biphenyl-2-ylcarbamic acid 1-[2-(2-chloro-4-formyl-5-methoxyphenyl-carbamoylethyl]piperidin-4-yl ester, wherein the first step is the reaction of methyl 4-(acryloylamino)-5-chloro-2-(methyloxy)benzoate with biphenyl-2-ylcarbamic acid piperidin-4-yl ester.

The object of the present invention is to provide a novel, alternative, more efficient and more economical process for the preparation of the compound of formula (II), a key intermediate in the preparation of biphenyl-2-ylcarbamic acid 1-[2-(2-chloro-4-{[(R)-2-hydroxy-2-(8-hydroxy-2-oxo-1,2-dihydroquinolin-5-yl)ethylamino]methyl}-5-methoxyphenylcarbamoyl)ethyl]piperidin-4-yl ester.

Thus according to the present invention there is provided a process for the preparation of the compound of formula (II):

(II)

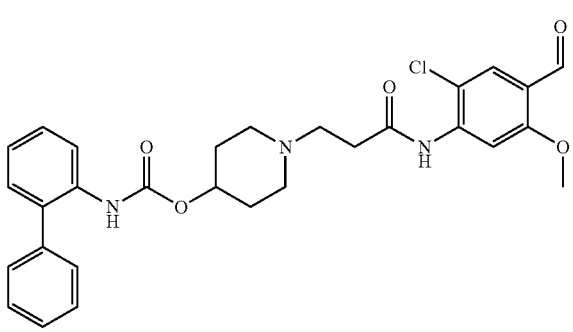

which process comprises reacting a compound of formula (VI):

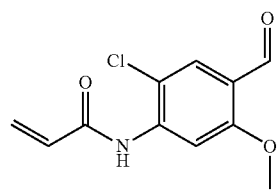

(VI)

with a compound of formula (IV):

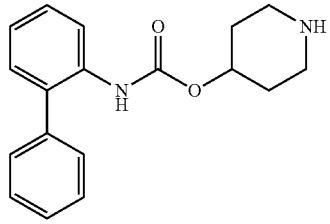

(IV)

in a suitable solvent.

This novel, alternative process results in a reduction in the number of steps required for the preparation of the compound of formula (II) from three steps to a single step, affording a number of advantages. Economically, the process results in a significant reduction in cycle time, reduced solvent waste and increased mass efficiency. In addition, the improved process addresses health and safety concerns by eliminating the use of the hazardous reducing reagents, lithium borohydride and lithium aluminium hydride and reduces the quantity of metal waste (manganese, lithium) in the process. Lithium borohydride is outlined in Preparation 96 (WO 2004/074246) and Preparation 5 (WO 2006/023454). Lithium aluminium hydride is outlined in Preparation 15 (WO 2006/023454). Manganese dioxide is outlined in Preparation 16 (WO 2006/023454) and Example 1 (WO 2007/090859).

The unexpected stability of the compound of formula (VI) coupled with its unpredicted reaction selectivity when treated with the compound of formula (IV) has enabled this single step process to be successfully developed.

The reaction between the compound of formula (VI) and the compound of formula (IV) is carried out in a suitable solvent. Suitable solvents may include aprotic and protic solvents.

Examples of suitable aprotic solvents include, but are not limited to, acetonitrile, 2-methyltetrahydrofuran, tetrahydrofuran, ethyl acetate, dimethylformamide and toluene. Examples of suitable protic solvents include, but are not limited to, ethanol, methanol, isopropyl alcohol and phenol. In a further aspect of the invention, the reaction is performed in 2-methyltetrahydrofuran as solvent.

The process may optionally further comprise the addition of a suitable organic acid source. Examples of suitable organic acids include organic carboxylic acids, such as acetic acid, formic acid and benzoic acid. The addition of a suitable organic carboxylic acid to the process improves the impurity profile of the reaction. Thus, in a further aspect of the invention the process further comprises addition of an organic acid source. In yet a further aspect of the invention the organic acid source is an organic carboxylic acid. In yet a further aspect of the invention the organic carboxylic acid is acetic acid.

The reaction may be performed at a temperature between ambient and the reflux temperature of the selected solvent, and maintained at this temperature until reaction is complete.

The product of the reaction may be crystallised from solution using a variety of standard crystallisation techniques, such as cooling crystallisation or anti-solvent addition crystallisation. In cooling crystallisation, the reaction mixture containing dissolved impure compound is cooled slowly, and optionally seeded, resulting in the formation of crystals of the required compound that will separate from the solution. After crystallisation, the crystals can be isolated by filtration, washed using a suitable solvent, and dried.

In a further aspect of the invention, where the reaction has been performed in 2-methyltetrahydrofuran, as solvent, with the addition of acetic acid, as an organic acid source, the reaction mixture is cooled to 60° C., seeded with biphenyl-2-ylcarbamic acid 1-[2-(2-chloro-4-formyl-5-methoxyphenylcarbamoylethyl]piperidin-4-yl ester, aged at 60° C. for 30 mins and then cooled to 20° C. over a period of 4 hours.

Anti-solvent addition crystallisation can be used as an alternative to cooling crystallisation for the separation and purification of the compound of interest. In anti-solvent addition crystallisation, the impure compound is dissolved in a suitable solvent. Addition of an anti-solvent reduces the solubility of the compound of interest in solution promoting the formation of crystals of the required compound. After crystallisation, the crystals can be isolated by filtration, washed using a suitable solvent, and dried.

In a further aspect of the invention, where the reaction has been performed in toluene, as solvent, the reaction mixture is concentrated at 50° C., and denatured ethanol antisolvent added to effect crystallisation. The mixture is aged at 60° C. for 4 hours and then cooled to 20° C. over a period of 4 hours.

In a further aspect of the invention there is provided a compound of formula (VI):

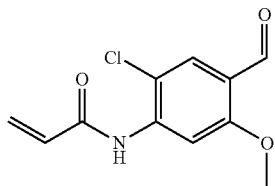

(VI)

In yet a further aspect of the invention there is provided N-[2-chloro-4-formyl-5-(methyloxy)phenyl]-2-propenamide.

EXPERIMENTAL

The invention is illustrated in the following example.

EXAMPLE

Step A: Preparation of 4-Bromo-2-chloro-5-methoxyaniline

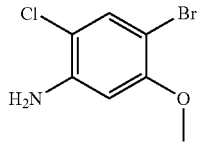

1,3-Dibromo-5,5-dimethylhydantoin (commercially available, for example, from Aldrich) (9.1 g, 32 mmol) was added over 20 minutes to a stirred solution of 6-chloro-3-methoxyaniline (commercially available, for example, from Apollo Scientific) (10.0 g, 63 mmol) in ethyl acetate (150 ml) at −5° C. The resulting solution was stirred at −5° C. for 1 hour then washed with a solution of potassium carbonate (6 g, 43 mmol) in water (40 ml and then with water (20 ml). The resulting solution was concentrated under reduced pressure to give 4-bromo-2-chloro-5-methoxyaniline as a pale brown solid (14.3 g, 95%).

$^1$H NMR (400 MHz, CDCl$_3$) $\delta_H$ (ppm) 7.38 (1H, s), 6.34 (1H, s), 4.02-4.14 (2H, br s), 3.83 (3H, s)

m/z (ES+) 236 (M+H)

Step B: Preparation of 4-Amino-5-chloro-2-methoxybenzaldehyde

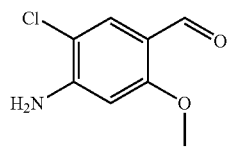

Isopropylmagnesium chloride (2M in tetrahydrofuran, 23 ml, 46 mmol) (commercially available, for example, from Aldrich) was added over 5 minutes to a stirred solution of 4-bromo-2-chloro-5-methoxyaniline (Step A) (10 g, 42 mmol) in tetrahydrofuran (70 ml) at −10° C. The resulting solution was allowed to warm to 0° C. over 50 minutes to give a thick slurry, then cooled to −25° C. and n-butyllithium (1.6M in hexanes, 90 ml, 144 mmol) was added over 20 minutes followed by tetrahydrofuran (20 ml). The solution was warmed to −10° C. over 30 minutes and then N,N-dimethylformamide (16 ml, 207 mmol) was added over 5 minutes and the resulting thick slurry was warmed to 0° C. over 20 minutes. A solution of citric acid (22 g, 105 mmol) in water (50 ml) was added cautiously over 15 minutes keeping reaction at <10° C. The slurry was aged at 20° C. for 30 minutes then filtered under vacuum. The cake was washed with water (100 ml) and then dried under vacuum at 40° C. for 16 hours to give 4-amino-5-chloro-2-methoxybenzaldehyde (6.1 g, 80% th) as a pale yellow solid.

$^1$H NMR (400 MHz, DMSO-d$_6$) $\delta_H$ (ppm) 9.95 (1H, s), 7.49 (1H, s), 6.50-6.57 (2H, br s), 6.44 (1H, s), 3.81 (3H, s)

m/z (ES+) 186 (M+H)

Step C: Preparation of N-[2-chloro-4-formyl-5-(methyloxy)phenyl]-2-propenamide

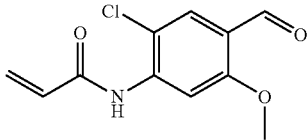 [SMILES: C=CC(=O)Nc1cc(OC)c(C=O)cc1Cl]

Preparation 1

Acrylic acid (commercially available, for example, from Aldrich) (46 ml, 0.67 mol) was added slowly to a stirred suspension of 4-amino-5-chloro-2-methoxybenzaldehyde (Step B) (50.0 g, 0.27 mol) and triethylamine (204 g, 2.02 mol) in ethyl acetate (0.85 L) at 25° C. Propanephosphonic anhydride (50% in ethyl acetate; 429 g, 0.67 mol) was added over 30 minutes keeping reaction temperature at 30-40° C. The mixture was stirred at 30-40° C. for a further 1 hour and then cooled to 25° C. and diluted with water (0.26 L) and acidified with 32% hydrochloric acid (108 g) to pH 2-3. The organic layer was separated and washed with a mixture of water (0.23 L) and 32% sodium hydroxide (14 g)—aqueous layer ca. pH 7. The organic phase was washed with water (0.23 L) and then concentrated under reduced pressure (ca. 300 mbar) to remove 0.56 kg of distillate. Methylcyclohexane (335 g) was added and then a further 286 g of distillate was removed under reduced pressure. Methylcyclohexane (111 g) was added and then the resulting suspension was cooled to 20° C., filtered and washed with methylcyclohexane. The cake was dried at 40° C. under reduced pressure for 12 hours to give N-[2-chloro-4-formyl-5-(methyloxy)phenyl]-2-propenamide (46 g, 71%)

Preparation 2

3-Chloropropionyl chloride (98.4 ml, 1.0 mol) was added over 30 minutes to a stirred suspension of 4-amino-5-chloro-2-methoxybenzaldehyde (47.4 g, 0.26 mol) ensuring the reaction temperature did not exceed 20° C. After the addition was complete the reaction was stirred at 20° C. for a further 2 hours and then filtered. The filtrate was concentrated to 150 ml under reduced pressure and then diluted with ethyl acetate (100 ml) and water (400 ml). The mixture was stirred at 20° C. for 1 hour and then filtered to give 3-chloro-N-[2-chloro-4-formyl-5-(methyloxy)phenyl]propanamide as an off-white solid which was not isolated but suspended in tetrahydrofuran (730 ml) and treated with diisopropylethylamine (154 ml, 0.88 mol). The resulting mixture was stirred at 45° C. for 46 hours and then concentrated under reduced pressure to leave a residue which was diluted with ethyl acetate (300 ml), washed with 2M hydrochloric acid (4×100 ml) and concentrated under reduced pressure to give N-[2-chloro-4-formyl-5-(methyloxy)phenyl]-2-propenamide (37.8 g, 62%).

$^1$H NMR (400 MHz, CDCl$_3$) $\delta_H$ (ppm) 10.31 (1H, s), 8.43 (1H, s), 8.02 (1H, br s), 7.82 (1H, s), 6.47-6.53 (1H, dd), 6.28-6.38 (1H, dd), 5.88-5.93 (1H, dd), 3.96 (3H, s)

m/z (ES+) 240 (M+H)

Step D: Preparation of Biphenyl-2-ylcarbamic acid 1-[2-(2-chloro-4-formyl-5-methoxyphenyl-carbamoylethyl]piperidin-4-yl ester

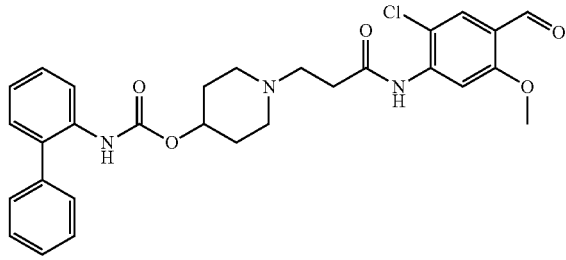 [SMILES: COc1cc(NC(=O)CCN2CCC(OC(=O)Nc3ccccc3-c3ccccc3)CC2)c(Cl)cc1C=O]

Preparation 1

Biphenyl-2-ylcarbamic acid piperidin-4-yl ester (which may be prepared according to preparation 8 in WO 2004/074246A) (1.03 kg, 3.48 mol) was added portionwise over 5 minutes to a stirred solution of N-[2-chloro-4-formyl-5-(methyloxy)phenyl]-2-propenamide (which may be prepared according to Step C (Preparation 1) or C (Preparation 2)) (0.81 kg, 3.38 mol) and acetic acid (0.39 L, 6.62 mol) in 2-methyltetrahydrofuran (8.1 L) at 60° C. The resulting solution was heated to 75° C. and held at this temperature for 2 hours. The solution was cooled to 60° C., seeded with biphenyl-2-ylcarbamic acid 1-[2-(2-chloro-4-formyl-5-methoxyphenyl-carbamoylethyl]piperidin-4-yl ester (4.0 g), aged at 60° C. for 30 mins and then cooled to 20° C. over 4 hours. The resulting suspension was filtered under vacuum and the filter cake was washed with IMS (3×1.6 L). The solid was dried in a vacuum oven at 50° C. for 10 hours to give biphenyl-2-ylcarbamic acid 1-[2-(2-chloro-4-formyl-5-methoxyphenyl-carbamoylethyl]piperidin-4-yl ester as a white solid (1.50 kg, 82% th).

$^1$H NMR (400 MHz, DMSO-d$_6$) $\delta_H$ (ppm) 10.70 (1H, s), 10.19 (1H, s), 8.68 (1H, s), 8.25 (1H, s), 7.72 (1H, s), 7.43-7.28 (9H, m), 4.48-4.54 (1H, br m), 3.88 (3H, s), 2.70-2.82 (2H, br s), 2.63 (4H, s), 2.20-2.30 (2H, br m), 1.72-1.82 (2H, br m), 1.49-1.56 (2H, br m)

m/z (ES+) 536 (M+H)

Preparation 2

Biphenyl-2-ylcarbamic acid piperidin-4-yl ester (which may be prepared according to preparation 8 in WO 2004/074246A) (63.0 kg, 212.57 mol) was added to a stirred suspension of N-[2-chloro-4-formyl-5-(methyloxy)phenyl]-2-propenamide (which may be prepared according to Step C (Preparation 1) or C (Preparation 2)) (50.0 kg, 208.62 mol) and acetic acid (12.6 kg, 209.83 mol) in 2-methyltetrahydrofuran (430 kg) at 25° C. The mixture was then heated to 50° C. over 60 mins and held at this temperature for 2 hours. The resulting suspension was cooled to 20° C. over 90 mins and held at this temperature for 4 hours. The suspension was filtered under vacuum and the filter cake was washed with IMS (3×78.9 kg). The solid was dried in a vacuum oven at 50° C. for 10 hours to give biphenyl-2-ylcarbamic acid 1-[2-(2-chloro-4-formyl-5-methoxyphenyl-carbamoylethyl]piperidin-4-yl ester as a white solid (90.7 kg, 80.6% th).

IR peak wavenumber (cm$^{-1}$) 3413, 2775, 1731, 1698, 1677, 1575, 1515, 1443, 1447, 1401, 1376, 1206, 1043, 1001, 758, 702

LC Rt=4.58 min

Equipment $^1$H NMR spectra were recorded on a Bruker DPX400, 400 MHz instrument in either CDCl$^3$ or DMSO-d6.

Mass spectra were recorded on a Waters LCT mass spectrometer operating in positive ion electrospray, mass range 100-1000 (ZQ) or 150-1500 (LCT) amu.

IR spectra were recorded as an ATR solid sample on a Perkin Elmer Spectrum 100 FTIR instrument, using 16 accumulations at a resolution of 2.0 cm$^{-1}$.

ATR=attenuated total reflectance

HPLC chromatograms were recorded on an Hewlett Packard Agilent 1100 series HPLC with the following conditions:

| Analytical Column | Luna C18, 50 × 2.0 mm (i.d.) 3 um | | |
|---|---|---|---|
| Mobile Phase | A = 0.05% v/v formic acid in water | | |
| | B = 0.05% v/v formic acid in acetonitrile | | |
| Flow Rate | 1 mL/min | | |
| Gradient Profile | Time | % A | % B |
| | 0 | 100 | 0 |
| | 8.00 | 5 | 95 |
| | 8.01 | 100 | 0 |
| | 11.00 | 100 | 0 |
| Temperature | 40° C. | | |
| Detection | UV, 230 nm | | |
| Injection Volume | 1 µL | | |
| Approximate Run Time | 11 mins | | |

The invention claimed is:

1. A process for the preparation of the compound of formula (II):

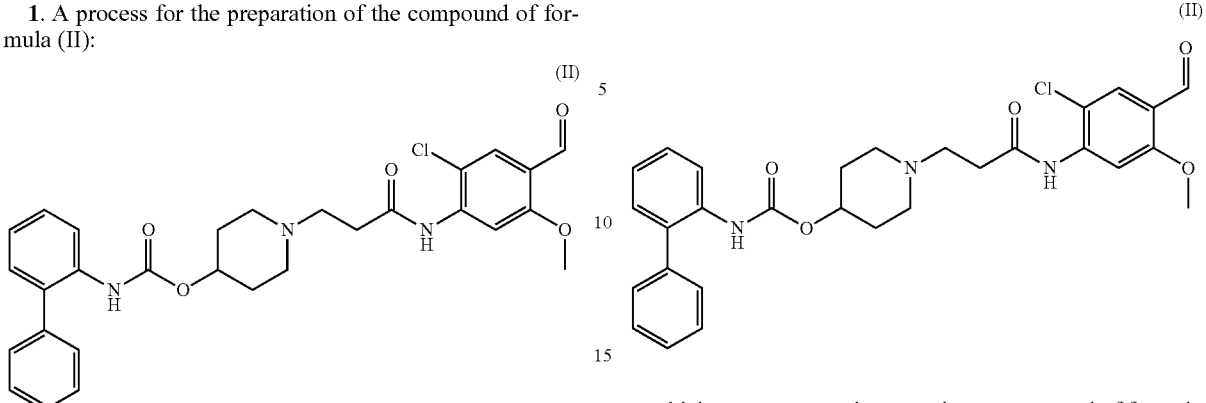

which process comprises reacting a compound of formula (VI):

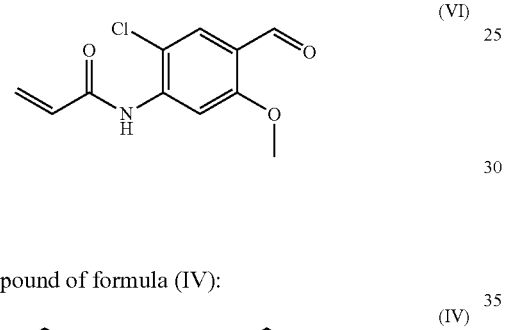

with a compound of formula (IV):

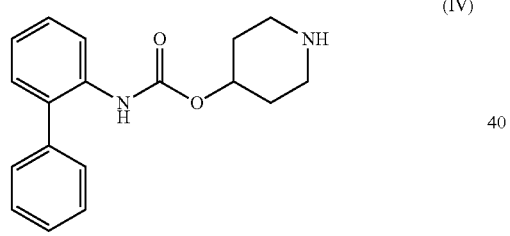

in a suitable solvent, selected from acetonitrile, 2-methyltetrahydrofuran, tetrahydrofuran, ethylacetate, dimethylformamide, toluene, ethanol, methanol, isopropanol and phenol.

2. A process according to claim 1 wherein the reaction is performed in an aprotic solvent.

3. A process according to claim 2 wherein the aprotic solvent is 2-methyltetrahydrofuran.

4. A process according to claim 1 wherein the process further comprises the addition of an organic carboxylic acid source.

5. A process according to claim 4 wherein the organic carboxylic acid, selected from formic acid, acetic acid and benzoic acid.

6. A process according to claim 5 wherein the organic carboxylic acid is acetic acid.

7. A process according to claim 1 wherein the reaction is performed at a temperature between ambient and the reflux temperature of the selected solvent.

8. A process according to claim 1 for the preparation of the compound of formula (II):

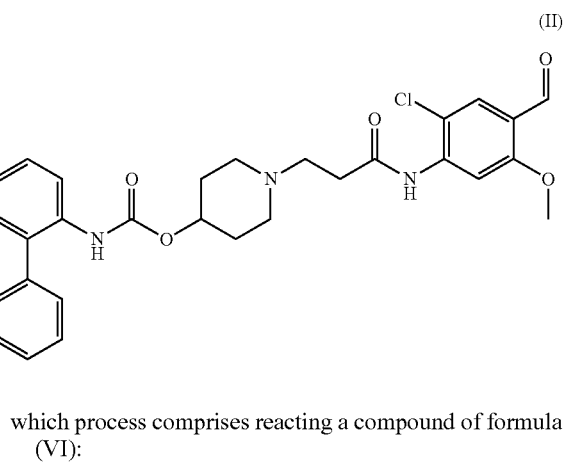

which process comprises reacting a compound of formula (VI):

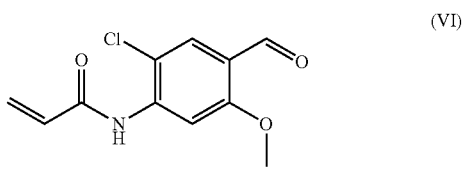 [SMILES: C=CC(=O)Nc1cc(OC)c(C=O)cc1Cl]

with a compound of formula (IV):

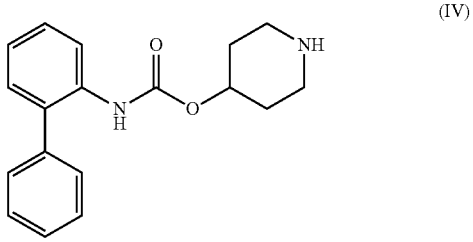 [SMILES: O=C(Nc1ccccc1-c1ccccc1)OC1CCNCC1]

in the presence of 2-methyltetrahydrofuran, as solvent, and acetic acid, as an organic carboxylic acid source, wherein the reaction is performed at a temperature of 75° C.

9. A process according to claim 8 wherein post reaction the reaction mixture is cooled to 60° C., seeded with biphenyl-2-ylcarbamic acid 1-[2-(2-chloro-4-formyl-5-methoxyphenylcarbamoylethyl]piperidin-4-yl ester, aged at 60° C. for 30 mins and then cooled to 20° C. over 4 hours.

10. A process according to claim 1 for the preparation of the compound of formula (II):

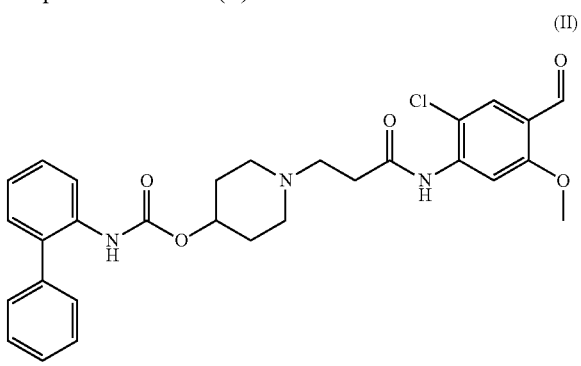

which process comprises reacting a compound of formula (VI):

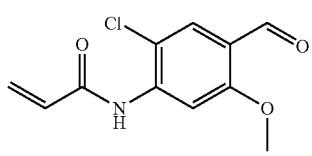

with a compound of formula (IV):

(IV)

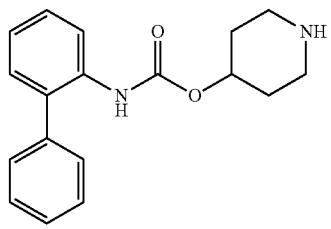

in the presence of 2-methyltetrahydrofuran, as solvent, and acetic acid, as an organic carboxylic acid source, wherein the reaction is performed at a temperature of 50° C.

11. A process according to claim 10 wherein post reaction the reaction mixture is cooled to 20° C. over 90 minutes, and then maintained at 20° C. for 4 hours.

12. A compound of formula (VI):

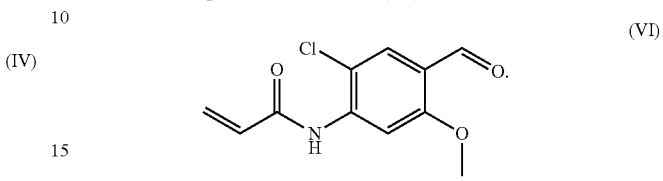

13. N-[2-chloro-4-formyl-5-(methyloxy)phenyl]-2-propenamide.

* * * * *